United States Patent [19]

Ulbrich et al.

[11] Patent Number: 5,589,624
[45] Date of Patent: Dec. 31, 1996

[54] ANTIFUNGAL POLYPEPTIDE AND PROCESS FOR ITS PRODUCTION

[75] Inventors: Norbert Ulbrich, Berlin; Rolf Hilgenfeld, Friedrichsdorf; Heinz Hänel, Oberursel; Burkhard Sachse, Kelkheim; Peter Braun, Mainz; Joachim Wink, Rödermark; Peter Eckes, Kelkheim; Jürgen Logemann; Jozef Schell, both of Köln, all of Germany

[73] Assignee: Hoechst Aktiengesellschaft, Germany

[21] Appl. No.: 372,455

[22] Filed: Jan. 13, 1995

Related U.S. Application Data

[62] Division of Ser. No. 945,982, Oct. 30, 1992, Pat. No. 5,421,839.

[30] Foreign Application Priority Data

Jun. 15, 1990 [DE] Germany .......................... 40 19 105.2
Mar. 6, 1991 [DE] Germany .......................... 41 07 140.9

[51] Int. Cl.$^6$ .................. C12N 5/04; C12N 5/10; C12N 15/09; C12N 15/31; A01H 1/00; A01H 5/00
[52] U.S. Cl. .............. 800/205; 47/58; 435/69.1; 435/70.1; 435/172.3; 435/240.4; 435/240.48; 435/240.49; 530/823; 536/23.74
[58] Field of Search .................. 435/69.1, 70.1, 435/172.1, 172.3, 240.48, 240.49, 240.5; 514/1; 530/820, 823; 47/58.03, 58.01, 58, DIG. 1; 800/200, 205, 250, 255, DIG. 43, 44; 536/23.74

[56] References Cited

U.S. PATENT DOCUMENTS 3,104,204 9/1963 Olson .
4,394,443 7/1983 Weissman et al. .
5,421,839 6/1995 Ulbrich et al. .................. 47/58

FOREIGN PATENT DOCUMENTS 0320130 6/1989 European Pat. Off. .
WO88/00976 2/1988 WIPO .
WO89/04371 5/1989 WIPO .

OTHER PUBLICATIONS

Applied Microbiology, vol. 13, No. 3, May 1965, pp. 314–321; Olson, B. H. et al.: 'Alpha sarcin, a new antitumor agent'.
Nucleic Acids Research, 18:13 (1990) Arlington, VA US p. 3987, Wnendt et al.: 'Cloning and nucleotide sequence of a cDNA encoding the antifungal–protein of *Aspergillus giganteus* and preliminary characterization of the native gene'.
J. Cell.Biochem.Suppl, vol. 14E, 1990, & Symposium Apr. 16–22, 1990, p. 268, Broglie, R., et al.: Chitinase expression in transgenic plants: increased protection against a soil--borne fungal pathogen.
Eur.J.Biochem, vol. 193, No. 1, 1990, pp. 31–38; Nakaya, K., et al.: 'Amino acid sequence and disulfide bridges of an antifungal–protein isolated from *Aspergillus giganteus*'.
An et al., 1986, Plant Physiol. 81:301–305.
An et al., 1985, Plant Physiol 79:568–570.
Potrykus, 1991, Annu. Rev. Plant Physiol, Plant Mol. Bio. 42:205–225.

*Primary Examiner*—Erich E. Veitenheimer
*Attorney, Agent, or Firm*—Curtis, Morris & Safford, P.C.

[57] ABSTRACT

The polypeptide with the sequence (SEQ ID NO: 1)

Ala—Thr—Tyr—Asn—Gly—Lys—Cys—Tyr—Lys—Lys—Asp—
Asn—Ile—Cys—Lys—Tyr—Lys—Ala—Gln—Ser—Gly—Lys—
Thr—Ala—Ile—Cys—Lys—Cys—Tyr—Val—Lys—Lys—Cys—
Pro—Arg—Asp—Gly—Ala—Lys—Cys—Glu—Phe—Asp—Ser—
Tyr—Lys—Gly—Lys—Cys—Tyr—Cys can be produced by the fermentation of *Aspergillus giganteus* and used as an antifungal agent.

Expression of this polypeptide gene in plants strongly inhibits the growth of phytopathogenic fungi on the plant.

19 Claims, No Drawings ial No. 07/945,982, filed Oct. 30, 1992, now U.S. Pat. No. 5,421,839.

ANTIFUNGAL POLYPEPTIDE AND PROCESS FOR ITS PRODUCTION

This application is a division of application Ser. No. 07/945,982, filed Oct. 30, 1992, now U.S. Pat. No. 5,421,839.

DESCRIPTION

Antifungal polypeptides, e.g. lectins, have been isolated from monocotyledonous and dicotyledonous plants [Ramshaw, J. A. M. (1982) in Nucleic Acids and Proteins in Plants I. Encyclopedia of Plant Physiology, New Series, (Boulter, D. and Parthier, B. editors.) vol. 14 A, pp. 229–279, Springer, Berlin]. It has also been observed that the biosynthesis of thionine is initiated by infestation of the plant with pathogenic fungi. It is therefore assumed that this protein possesses antifungal activity [Bohlmann, H. et al. (1989) EMBO J. 7, 1559–1565; Broekaert, W. F. et al. (1989) Science 245, 1100–1102].

Antifungal polypeptides have also been isolated from microorganisms. For example, a similar protein has been detected in the fermentation broth of *Aspergillus giganteus* (Olson, B. M. & Goerner, G. L. (1965) Appl. Microbiol. 13, 314–321), but the amino acid sequence of said protein is two lysine residues shorter than that of the protein according to the invention.

We have now been able to isolate a polypeptide with antifungal action from *Asperillus giganteus* and determine its sequence.

The nucleotide sequence of the peptide claimed has been published by Wnendt et al. (Nucl. Acids Res. 18, p. 3987, September 1990).

We have moreover found that expression, in plants, of the gene which codes for the polypeptide claimed in the main patent application cited above strongly inhibits the growth of phytopathogenic fungi on the plant.

The invention thus relates to:

A polypeptide with the amino acid sequence (SEQ ID NO: 1)

Ala—Thr—Tyr—Asn—Gly—Lys—Cys—Tyr—Lys—Lys—Asp—Asn—Ile—

Cys—Lys—Tyr—Lys—Ala—Gln—Ser—Gly—Lys—Thr—Ala—Ile—Cys—

Lys—Cys—Tyr—Val—Lys—Lys—Cys—Pro—Arg—Asp—Gly—Ala—Lys—

Cys—Glu—Phe—Asp—Ser—Tyr—Lys—Gly—Lys—Cys—Tyr—Cys.

A process for the production of the polypeptide characterized above, which process is characterized in that *Aspergillus giganteus* is cultivated and the polypeptide is isolated.

Use of the polypeptide as an antifungal agent.

A plant cell which expresses the gene of the antifungal peptide from *Aspergillus giganteus*, as well as a plant containing such cells, and plants, plant tissue or plant reproductive material grown from such a cell.

A process for the production of the plant cell, characterized in that the gene of the antifungal polypeptide from *Aspergillus giganteus* is expressed in the plant cell.

The invention is described in detail below, especially in its preferred embodiments. The invention is further determined by the content of the claims.

The polypeptide according to the invention is synthesized from *Aspergillus giganteus* with aerobic cultivation. Assimilable carbohydrates and sugar alcohols such as fructose, lactose or mannitol, and natural products containing carbohydrate, are suitable as preferred carbon sources. The following are possible as preferred nitrogenous nutrients: antino acids, peptides and proteins, as well as degradation products thereof, such as peptones or tryptones, and also meat extracts, ground seeds, for example of maize, wheat, beans, soya or the cotton plant, distillation residues from alcohol production, meat meals or yeast extracts, or else ammonium salts and nitrates. The nutrient solution can also contain for example chlorides, carbonates, sulfates or phosphates of the alkali metals or alkaline earth metals, iron, zinc and manganese, as additional inorganic salts.

The formation of the compound of the polypeptide according to the invention proceeds particularly well in a nutrient solution containing 0.5 to 2% of meat extracts, 0.5 to 2% of peptone, 0.5 to 4% of starch and 0.1 to 1% of sodium chloride, based in each case on the weight of the total nutrient solution.

The fermentation takes place aerobically, for example submersed with shaking or stirring in shake flasks or fermenters, with air or oxygen being introduced if appropriate. It can be carried out over a temperature range of about 18° to 35° C., preferably at about 25° to 30° C. The microorganism is cultivated under said conditions until the stationary phase is reached, i.e. for about 70 to 80 hours.

The cultivation is advantageously carried out in several stages, i.e. one or more initial cultures are first prepared in a liquid nutrient medium and then inoculated into the actual production medium—the main culture—for example in a volume ratio of 1:10. The initial culture is obtained for example by inoculating a sporulated mycelium into a nutrient solution and leaving it to grow for about 48 to 72 hours. The sporulated mycelium can be obtained by leaving the strain to grow for about 7 days on a solid or liquid culture medium, for example malt agar.

The course of the fermentation can be monitored by means of the pH of the culture or the volume of the mycelium, by thin layer chromatography, by testing the biological activity or by an immunological method.

The isolation of the polypeptide from the culture medium is effected by known methods, taking into account the chemical, physical and biological properties of the products. The polypeptide is present in the culture broth.

The broth is freed from mycelium and then chromatographed on a cation exchanger. After dialysis and concentration, gel filtration is carried out, preferably on an agarose/acrylamide copolymer. The subsequent thorough purification of the polypeptide, which is necessary for the sequence analysis, can be carried out by HPLC using a linear gradient on a column with hydrophobic interaction.

The enzymatic digestion of the peptide for elucidation of the amino acid sequence is carried out by methods known per se and results in the amino acid sequence given above. Heat stability is a characteristic of the enzyme. It shows no loss of activity after heating at 100° C. for a period of 20 minutes.

The protein can be used as an antifungal agent, especially against phytopathogenic fungi. The invention therefore also relates to a composition for inhibiting or destroying phytopathogenic fungi on plants, which is characterized in that it contains protein according to the invention. Phytopathogens can be successfully controlled in both a protective and a curative capacity. The spectrum of action of the claimed compound includes a large number of different phytopathogenic fungi of economic importance, e.g. *Piricularia oryzae, Venturia inaequalis, Cercospora beticola,* true mildew species, Fusarium species, *Plasmopora viticola, Pseudoperonospora cubensis,* various rust fungi and *Pseudocercosporella herpotrichoides.* Benzimidazole- and dicarboximide-sensitive and -resistant *Botrytis cinerea* strains are included in particular.

The compound according to the invention is also suitable for use in industrial sectors, for example as a preservative for industrial products and foodstuffs or feedingstuffs.

The invention further relates to compositions containing the above-mentioned compound in addition to suitable formulation aids.

The individual types of formulation are known to those skilled in the art and are described for example in: Winnacker-Küchler, "Chemische Technologie" ("Chemical Technology"), volume 7, C. Hanser Verlag Munich, 4th edition 1986; van Falkenberg, "Pesticides Formulations", Marcel Dekker N.Y., 2nd edition, 1972–73; K. Martens, "Spray Drying Handbook", 3rd edition, 1979, G. Goodwin Ltd. London.

The necessary formulation aids, such as inert materials, surfactants, solvents and other additives, are also known and are described for example in: Watkins, "Handbook of Insecticide Dust Diluents and Carriers", 2nd edition, Darland Books, Caldwell N. J.; H. v. Olphen, "Introduction to Clay Colloid Chemistry", 2nd edition, J. Wiley & Sons, N.Y.; Marschen, "Solvents Guide", 2nd edition; Interscience, N.Y. 1950; McCutcheon's "Detergents and Emulsifiers Annual" MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" ("Surface-Active Ethylene Oxide Adducts"), Wiss. Verlagsgesell., Stuttgart 1976; Winnacker-Küchler, "Chemische Technologie" ("Chemical Technology"), volume 7, C. Hanser Verlag Munich, 4th edition 1986.

On the basis of these formulations, it is also possible to prepare combinations with other pesticidally active substances, fertilizers and/or growth regulators, e.g. in the form of a finished formulation or as a tank mix.

The following products may be mentioned as examples of fungicides known in the literature which can be combined, according to the invention, with the compound of formula I: anilazine, benalaxyl, benodanil, benomyl, binapacryl, bitertanol, buthiobat, captafol, captan, carbendazim, carboxin, CGD-94240 F, chlobenzthiazone, chlorthalonil, cymoxanil, cyproconazole, cyprofuram, dichlofluanid, dichlomezin, diclobutrazol, diethofencarb, difluconazole, dimethirimol, dimethomorph, diniconazole, dinocap, dithianon, dodemorph, dodine, edifenfos, ethirimol, etridiazol, fenarimol, fenfuram, fenpiclonil, fenpropidin, fenpropimorph, fentin acetate, fentin hydroxide, fluaziram, fluobenzimine, fluorimide, flusilazole, flutolanil, flutriafol, folpet, fosetyl aluminum, fuberidazole, furalaxyl, furmecyclox, guazatine, hexaconazole, imazalil, iprobenfos, iprodione, isoprothiolane, copper compounds such as copper oxychloride, copper oxine and copper oxides, mancozeb, maneb, mepronil, metalaxyl, methasulfocarb, methfuroxam, myclobutanil, nabam, nitrothalidopropyl, nuarimol, ofurace, oxadixyl, oxycarboxin, penconazol, pencycuron, PP 969, probenazole, probineb, prochloraz, procymidon, propamocarb, propiconazol, prothiocarb, pyracarbolid, pyrifenox, pyroquilon, rabenzazole, sulfur, tebuconazole, thiabendazole, thiofanate-methyl, thiram, tolclofos-methyl, tolylfluanid, triadimefon, triadimenol, tricyclazole, tridemorph, triflumizol, triforine, vinchlozolin, zineb, sodium dodecylsulfonate, sodium dodecylsulfate, sodium $C_{13}/C_{15}$-alkylether-sulfonate, sodium cetostearylphosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkylimidazoline.

The above-mentioned combination partners are known active ingredients, most of which are described in C. H. R. Worthing and U. S. B. Walker, The Pesticide Manual, 7th edition (1983), British Crop Protection Council.

Furthermore, the active ingredient according to the invention can be mixed with other active ingredients, such as insecticides, attractants, sterilizing agents, acaricides, nematicides or herbicides, in its commercially available formulations as well as in the use forms prepared from these formulations. The insecticides include for example phosphoric acid esters, carbamates, carboxylic acid esters, formamidines, tin compounds, substances produced by microorganisms, etc. Preferred mixing partners are:

1. From the group of the phosphorus compounds:
acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachloroethylphosphorthioate (SD 208 304), dimethoate, disulfoton, EPN, ethion, ethoprophos, etrimfos, famphur, fenaminphos, fenitriothion, fensulfothion, fenthion, fonofos, formothion, heptenophos, isozophos, isothioate, isoxathion, malathion, methacrifos, methamidophos, methidation, salithion, mevinphos, monocrotophos, naled, omethoate, oxydemeton-methyl, parathion, parathionmethyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon and vamidothion;

2. From the group of the carbamates:
aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, primicarb, propoxur, thiodicarb, thiofanox, ethyl 4,6,9-triaza-4-benzyl-6,10-dimethyl-8-oxa-7-oxo- 5,11-dithia-9-dodecenoate (OK 135) and 1-methylthio(ethylideneamino) N-methyl-N-(morpholinothio)carbamate (UC 51717);

3. From the group of the carboxylic acid esters:
allethrin, alphamethrin, 5-benzylfuryl-3-methyl (E)-(1R)-cis-2,2-dimethyl-3-(2-oxothiolan-3-ylidenemethyl)cyclopropanecarboxylate, bioallethrin, bioallethrin ((S)-cyclopentyl isomer), bioresmethrin, biphenate, (RS)-1-cyano-1-(6-phenoxypyrid-2-yl)methyl (1RS)-trans- 3-(4-tert-butylphenyl)-2,2-dimethylcyclopropanecarboxylate (NCI 85193), cycloprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R)isomer), d-pralethrin, pyrethrins (natural products), resmethrin, tefluthrin, tetramethrin and tralomethrin;
4. From the group of the amidines:
   amitraz and chlordimeform;
5. From the group of the tin compounds:
   cyhexatin and fenbutatin oxide;
6. Miscellaneous:
   abamectin, *Bacillus thuringiensis*, bensultap, binapacyl, bromopropylate, buprofezin, camphechlor, cartap, chlorbenzialate, chlorfluazuron, 2-(4-chlorphenyl)-4,5-diphenylthiophene (UBI-T 930), chlofentezine, naphthyl-2-methyl cyclopropanecarboxylate (Ro 12-0470), cyromazin, ethyl N-(3,5-dichloro-4-(1,1,2,3,3,3-hexafluoro-1-propoxy)phenyl)carbamoyl-2-chlorobenzcarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217 300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108 477), propargite, teflubenzuron, tetradifon, tetrasul, thicyclam and triflumaron.

Unless indicated otherwise, all gene technology work on the expression of the gene in plants was carried out in accordance with the methods described in "Molecular Cloning" (Maniatis et al., Cold Spring Harbor, 1982).

Unless indicated otherwise, all the enzymes used were obtained from Boehringer Mannheim. The chemicals Originate from Merck (Darmstadt).

For cloning in the vector, the cDNA sequence of the antifungal peptide is provided with ends which can be ligated at BamHI and SalI restriction cleavage sites.

The cloning vector used was pDH 51 (Pietrzak et al., Nucl. Acids Res. 14, p. 5857, 1986).

Vector pDH 51 is opened with the restriction enzymes BamHI and SalI between promoter and terminator. Vector pDH 51 is a pUC 18 derivative which contains promoter and terminator sequences of the 35S transcript from cauliflower mosaic virus. These sequences are recognized by the plant's transcription apparatus and result in strong constitutive expression of their associated gene in plants.

Apart from the 35S promoter, it is possible to use any other promoter which is effective in plants.

The DNA of the antifungal peptide is then cloned into the vector via the BamHI and SalI cleavage sites so that the promoter sequence is located upstream and the terminator sequence downstream.

The transcription unit comprising promoter, gene and terminator is cut out of the vector with the restriction enzyme EcoRI and cloned into a plant transformation vector.

The following vectors and derivatives thereof are examples of plant transformation vectors which can be used:
—pOCA 18 (Olszewski et al., Nucl. Acids Res. 16, p. 10765, 1988) and
—pPCV 310 (Koncz and Schell, MGG 204, p. 383, 1986).

It is also possible to use any other plant transformation vector possessing the border sequence of the Ti plasmid of *Agrobacterium tumefaciens,* which is important for an insertion into the genome of plants.

After the transcription unit and vector have been ligated via the EcoRI cleavage site, the construct is conjugated into the Agrobacterium strain MP90RK (Koncz and Schell, MGG 204, p. 383, 1986) or EHA 101 (Hood et al., J. Bacteriol. 168, p. 1291, 1986).

The method of conjugation is described in "Plant Molecular Biology/Manual" (Kluwer Academic Publisher, Dordrecht, 1988).

Tobacco and tomato plants are transformed by the leaf disc method (Horsch et al., Science 227, 1229 (1985)). In principle, it is also possible to transform any other dicotyledonous plant. Transformed buds are selected on the basis of the transferred resistance to the antibiotic kanamycin. Expression of the antifungal protein in the transformed production plants is checked by DNA analysis (Southern blotting), RNA analysis (Northern blotting) and protein analysis with specific antibodies (Western blotting).

Monocotyledonous plants are transformed by means of direct gene transfer into protoplasts. These protoplasts are then regenerated into intact plants (Gene Transfer in Cereals, Potrykus I., Biotechnology 8, p. 535, 1990).

Plants which express the protein are transferred to the greenhouse and inoculated with phytopathogenic fungi. Inoculation is effected with a suspension of hyphae or conidiospores, depending on the species of fungi. The leaf stage of the plant which is to be used for inoculation, and the incubation time, depend on the plant and the phytopathogenic fungus.

The invention is illustrated in greater detail below with the aid of Examples.

EXAMPLES

1. Cultivation of *Aspergillus giganteus* a) Preparation of a spore suspension of the producer strain:

100 ml of nutrient solution (0.75% of meat extract, 1% of peptone, 2% of soluble starch and 0.5% of NaCl) in a 500 ml Erlenmeyer flask are inoculated with the strain and incubated on a rotary shaker for 72 hours at 25° C. and 120 rpm. Then 20 ml of culture fluid in a 500 ml Erlenmeyer flask containing the culture medium of the above-mentioned composition, to which 20 g of agar/l have been added to solidify the medium, are divided up into equal portions and decanted. The cultures are incubated for 10 to 14 days at 25° C. The spores which have formed in one flask after this time are rinsed with 500 ml of deionized water containing one drop of a commercially available non-ionic surfactant, and reused immediately or stored at −22° C.

b) Preparation of a culture or initial culture of the producer strain in an Erlenmeyer flask:

A 500 ml Erlenmeyer flask containing 100 ml of a nutrient solution of the above-mentioned composition (pH 6.5) is inoculated with a culture grown on a slant tube or with 0.2 ml of spore suspension and incubated on a shaker at 120 rpm and 25° C. The production maximum is reached after approx. 80 hours (pH=5.3). The yields are approx. 1 to 2 mg/l.

2. Isolation and Purification of the Polypeptide

The polypeptide is worked up according to Olson, B. M. & Goerner, G. L. (1965) Appl. Microbiol. 13, 314–321. The subsequent thorough purification is carried out by means of HPLC at a flow rate of 2 ml/min on an ODS-120T column (0.46×25 cm) with a linear gradient of 5 to 20% of acetonitrile (v/v) to which 0.1% of trifluoroacetic acid has been added.

3. Characterization of the Polypeptide a) Enzymatic cleavage:

For enzymatic cleavage, the polypeptide is incubated at 37° C. for a period of 2 hours in 1M Tris-HCl buffer (pH 8) to which 6M guanidine and 2 mM EDTA have been added, and reduced at 37° C. over a period of 12 hours by the addition of 0.1M dithiotritol. The reduced protein is then treated with 0.15M iodoacetamide at 37° C. for 20 minutes. The S-carboxyamidomethylated protein is separated from impurities by HPLC as described above and then treated with chymotrypsin (EC 3.4.21.1) in 0.1M ammonium bicarbonate buffer (pH 8) at 37° C. for 30 minutes.

The protein concentration is 150 µg/ml for an enzyme:substrate ratio of 1:50 (w/w).

Digestion with *Staphylococcus aurcus* V 8 protease (EC 3.4.21.15) is carried out in 0.1M bicarbonate buffer (pH 8) for 18 hours at 37° C., the enzyme: substrate ratio being 1:30 (w/w).

Treatment of the native or S-carboxymethylated protein with lysylendopeptidase (EC 3.4.21.50) is effected by incubation for 30 minutes at 37° C. in 8M urea to which 0.1M Tris-HCl (pH 9) has been added, followed by digestion in 0.1M Tris-HCl (pH 8) for 12 hours at 37° C. with an enzyme:substrate ratio of 1:100 (w/w).

Digestion of the S-carboxyamidomethylated protein with carboxypeptidase Y (EC 3.4.16.1) is carried out in 25 mM phosphate buffer (pH 6.5) at 37° C. for up to 4 hours, the enzyme:substrate ratio being 1:3 (w/w).

b) Amino acid analysis and sequence determination:

The protein and the fragments are hydrolyzed in 6N HCl for 22 hours at 110° C. The amino acid sequence analysis is carried out with an Applied Biosystems Protein Sequencer (model 470 A).

Phenylhydantoin amino acid derivatives are identified by HPLC (ODS-120T, 0.46×25 cm) according to Tsunasawa, S. et al., (1985) J. Biochem. (Tokyo) 97, 701–704. Phenylhydantoin Cam-Cys is determined as described in Theerasilp, S. et al., (1989) J. Biol. Chem. 264, 6655–6659.

c) Determination of cystine and cysteine fragments:

The analysis is performed by reaction with Ellman's reagent—5,5'-dithiobis(2-nitrobenzoic acid)—before and after treatment with sodium borohydride, according to Henschen, A. (1986) in Advanced Methods in Protein Microsequence Analysis (Wittmann-Liebold, B., Salnikow, J. & Erdmann, V. A., editors), pp. 244–255, Springer-Verlag, Berlin. The protein is incubated in water for 1 hour at 50° C. in the presence or absence of 2.5% of sodium borohydride. After subsequent destruction of the borohydride by treatment with 0.3N HCl for 30 minutes, the sample is incubated for 5 minutes with 0.11% of Ellman's reagent in 0.04M phosphate buffer (pH 8.1). The absorption is then measured at 412 nm.

Result:

The protein according to the invention has the following amino acid sequence (SEQ ID NO: 1):

Ala—Thr—Tyr—Asn—Gly—Lys—Cys—Tyr—Lys—Lys—Asp—Asn—Ile—

Cys—Lys—Tyr—Lys—Ala—Gln—Ser—Gly—Lys—Thr—Ala—Ile—Cys—

Lys—Cys—Tyr—Val—Lys—Lys—Cys—Pro—Arg—Asp—Gly—Ala—Lys—

Cys—Glu—Phe—Asp—Ser—Tyr—Lys—Gly—Lys—Cys—Tyr—Cys.

The sum of the molecular weights of the analyzed amino acids is 5788 Dalton.

4 disulfide bridges can be identified as follows:

Cys 7–Cys 33, Cys 14–Cys 40, Cys 26–Cys 28 and Cys 49–Cys 51

```
          7           9
    L4    Cys—Tyr—Lys (SEQ ID NO: 2)
          Cys—Pro—Arg—Asp—Gly—Ala—Lys (SEQ ID NO: 3)
          33                        39

23          27
    L9    Thr—Ala—Ile—Cys—Lys (SEQ ID NO: 4)
                        Cys—Tyr—Val—Lys (SEQ ID NO: 5)
                        28          31

11                15
    L10   Asp—Asn—Ile—Cys—Lys (SEQ ID NO: 6)
                        Cys—Glu—Phe—Asp—Ser—Tyr—Lys (SE1 ID NO: 7)
                        40                          46

49          51
    L8    Cys—Tyr—Cys (SEQ ID NO: 8)
```

4. Antifungal Activity

The antifungal activity is assessed according to Roether W. et al., Mykosen 27 (1), 14–28 (1984). The results are listed in Table 1 below.

TABLE 1

Minimum inhibitory concentration of the antifungal polypeptide according to the invention towards fungi in vitro (µg/ml)

| | |
|---|---|
| *Trichophyton mentagrophytes* | 125 |
| *Trichophyton rubrum* | 62.5 |
| *Microsporum canis* | 15.2 |

TABLE 1-continued

Minimum inhibitory concentration of the antifungal polypeptide according to the invention towards fungi in vitro (μg/ml)

| | |
|---|---|
| Candida albicans | >>125 |
| Aspergillus niger | 7.81 |
| Aspergillus tereus | 7.5 |
| Aspergillus fumigatus | 7.3 |
| Aspergillus nidulans | 7.4 |
| Aspergillus giganteus | 7.8 |
| Penicillium carylophilium | 7.9 |
| Fusarium aquaductum | 7.2 |
| Fusarium oxisporum | 7.3 |

5. Formulation Examples a) A dust is obtained by mixing 10 parts by weight of active ingredient and 90 parts by weight of talc as an inert material and comminuting the mixture in an impact pulverizer.

b) A wettable powder which is readily dispersible in water is obtained by mixing 25 parts by weight of active ingredient, 65 parts by weight of kaolin-containing quartz as an inert material, 10 parts by weight of potassium ligninsulfonate and 1 part by weight of sodium oleoylmethyltaurate as a wetting agent and dispersant and grinding the mixture in a pinned disc mill.

c) Granules can be prepared from 2 to 15 parts by weight of active ingredient and an inert granule carrier such as attapulgite, granulated pumice and/or quartz sand. It is convenient to use a suspension of the wettable powder from Example b) with a solids content of 30% and to spray this suspension on to the surface of granulated attapulgite, which is dried and intimately mixed. The proportion by weight of wettable powder here is approx. 5% and that of the inert carrier is approx. 95% of the finished granules.

6. Biological Examples

Approx. 14-day-old broad beans of the "Herz Freya" or "Frank's Ackerperle" variety were wetted uniformly with the polypeptide according to the invention in various concentration as a wettable powder formulation).

After the spray coating had dried on, the plants were inoculated with a spore suspension (1.5 million spores/ml) of *Botrytis cinerea* (BCM- and dicarboximide-sensitive strain=Table 2, BCM- and dicarboximide-resistant strain= Table 3). The plants were grown on in a climatic chamber at 20°–22° C. and approx. 99% relative humidity. Infection of the plants manifests itself in the formation of black spots on leaves and stems. The trials were evaluated approx. 1 week after inoculation.

The efficacy of the test substances was assessed as a percentage relative to the untreated infested control and is shown in Tables 2 and 3.

TABLE 2

Efficacy (in %) of polypeptide against BCM-dicarboximide sensitive as a percentage relative to untreated infested control plants

| | | | | | |
|---|---|---|---|---|---|
| Conc. (mg/l) of active ingredient (polypeptide) in spraying mixture | 500 | 250 | 125 | 60 | 30 |
| Efficacy in %: | | | | | |
| polypeptide-treated plants | 100 | 100 | 100 | 99 | 85 |
| untreated infested plants | 0 | 0 | 0 | 0 | 0 |

TABLE 3

Efficacy (in %) of polypeptide against BCM-dicarboximide resistant as a percentage relative to untreated infested controls

| | | | | | |
|---|---|---|---|---|---|
| Conc. (mg/l) of active ingredient (polypeptide) in spraying mixture | 500 | 250 | 125 | 60 | 30 |
| Efficacy in %: | | | | | |
| polypeptide-treated plants | 100 | 100 | 100 | 98 | 85 |
| untreated infested plants | 0 | 0 | 0 | 0 | 0 |

7. Inoculation of Transgenic Tomato Plants with *Botrytis cinerea*

Wild-type tomato plants and transgenic plants of the same variety were inoculated at the 5- to 6-leaf stage with conidiospores of *Botrytis cinerea* and then kept for 3–4 days at 20° C. and 99% relative humidity. The trial was then evaluated by visual assessment; the leaf area infested with *Botrytis cinerea* (olive-gray spots and wilting symptoms) of the transgenic plants was evaluated in comparison with that of the wild-type plants. The degree of infestation of the plants is shown in Table 4.

TABLE 4

| Tomato plants | Infestation with *Botrytis cinerea* in % infested leaf area |
|---|---|
| wild-type plants | 90–100 |
| transgenic plants | 30–60 |

8. Inoculation of Transgenic Tobacco Plants with *Scterontinia sclerotiorum*

Wild-type tobacco plants and transgenic plants of the same variety were inoculated at the 4-leaf stage with hyphae (suspension) of *Scterontinia sclerotiorum* and kept at approx. 25° C. and >90% relative humidity for approx. 3 days. The leaf area infested with *Scterontinia sclerotiorum* (glassy spots, leaf rot, mycelium deposits) of the transgenic experimental plants was then evaluated in comparison with that of the wild-type plants. The degree of infestation of the plants is shown in Table 5.

TABLE 5

| Tobacco plants | Infestation with *Scterontinia sclerotiorum* in % infested leaf area |
|---|---|
| wild-type plants | 100 |
| transgenic plants | 30–55 |

We claim:

1. A plant cell which expresses the polypeptide with the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile- Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID NO: 1).

2. A plant containing cells according to claim 1.

3. A plant grown from and containing a plant cell according to claim 1.

4. A process for the production of a viable plant cell, comprising transforming the cell so that it contains a gene coding for an antifungal polypeptide isolated from *Aspergillus giganteus* having the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID. NO: 1) wherein the polypeptide is expressed in the plant cell.

5. Plant tissue grown from and containing a plant cell according to claim 1.

6. Plant reproductive material grown from and containing a plant cell according to claim 1.

7. A plant cell which expresses the polypeptide with the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID NO: 1) which is a tobacco or tomato plant cell.

8. A plant containing cells which express the polypeptide with the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-pro-Arg-Asp-Gly-Ala-Lys-Cys-Glu-Phe-Asp-Ser-Tyr-Lys-Gly-Lys-Tyr-Cys (SEQ ID NO: 1) which is a tobacco or tomato plant.

9. A plant grown from and containing a plant cell which expresses the polypeptide with the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID NO: 1) which is a tobacco or tomato plant.

10. Plant tissue grown from and containing a plant cell which expresses the polypeptide with the amino acid Sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID NO: 1) which is tobacco or tomato plant tissue.

11. Plant reproductive material grown from and containing a plant cell which expresses the polypeptide with the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID NO: 1) which is tobacco or tomato plant reproductive material.

12. A process for the production of a viable plant cell, comprising transforming the cell so that it contains a gene coding for an antifungal polypeptide isolated from *Aspergillus giganteus* having the amino acid sequence Ala-Thr-Tyr-Asn-Gly-Lys-Cys-Tyr-Lys-Lys-Asp-Asn-Ile-Cys-Lys-Tyr-Lys-ala-Gln-Ser-Gly-Lys-Thr-Ala-Ile-Cys-Lys-Cys-Tyr-Val-Lys-Lys-Cys-Pro-Arg-Asp-Gly-Ala-Lys-Cys-Glu-Phe-Asp-Ser-Tyr-Lys-Gly-Lys-Tyr-Cys (SEQ ID. NO: 1) wherein the polypeptide is expressed in the plant cell and, the plant cell is a tomato or tobacco plant cell.

13. The process of claim 12 wherein the plant cell is a tomato plant cell.

14. The process of claim 12 wherein the plant cell is a tobacco plant cell.

15. The process of claim 4 wherein the plant cell is a dicotyledonous plant cell.

16. The process of claim 4 wherein the plant cell is a monocotyledonous plant cell.

17. The process of claim 15 wherein the transforming is by a leaf disc method.

18. The process of claim 16 wherein the transforming is by direct gene transfer into protoplasts.

19. The process of claim 12 wherein the transforming is an Agrobacterium-mediated transformation.

* * * * *

UNITED STATES PATENT AND TRADEMARK OFFICE
CERTIFICATE OF CORRECTION

PATENT NO. : 5,589,624
DATED : Dec. 31, 1996
INVENTOR(S) : Ulbrich et al

It is certified that error appears in the above-identified patent and that said Letters Patent is hereby corrected as shown below:

IN THE CLAIMS:

Claim 1, line 6, change "Lys-Tyr-Cys" to --Lys-Cys-Tyr-Cys--;

Claim 4, line 8, change "Asp-Ser-Tyr-Lys-Gly-Lys-Tyr-Cys" to --Asp-Ser-Tyr-Lys-Gly-Lys-Cys-Tyr-Cys--;

Claim 7, line 6, change "Lys-Tyr-Cys" to --Lys-Cys-Tyr-Cys--;

Claim 8, line 6, change "Lys-Gly-Lys-Tyr-Cys" to --Lys-Gly-Lys-Cys-Tyr-Cys--;

Claim 9, line 6, change "Cys-Glu-Phe-Asp-Ser-Tyr-Lys-Gly-Lys-Tyr-Cys" to --Cys-Glu-Phe-Asp-Ser-Tyr-Lys-Gly-Lys-Cys-Tyr-Cys--;

Claim 10, line 6, change "Lys-Cys-Glu-Phe-Asp-Ser-Tyr-Lys-Gly-Lys-Tyr-Cys" to --Lys-Cys-Glu-Phe-Asp-Ser-Tyr-Lys-Gly-Lys-Cys-Tyr-Cys--;

Claim 11, line 7, change "Lys-Tyr-Cys" to --Lys-Cys-Tyr-Cys--; and

UNITED STATES PATENT AND TRADEMARK OFFICE
CERTIFICATE OF CORRECTION

PATENT NO.  : 5,589,624
DATED       : Dec. 31, 1996
INVENTOR(S) : Ulbrich et al

It is certified that error appears in the above-identified patent and that said Letters Patent is hereby corrected as shown below:

<u>Claim 12, line 8</u>, change "Asp-Ser-Tyr-Lys-Gly-Lys-Tyr-Cys" to --Asp-Ser-Tyr-Lys-Gly-Lys-Cys-Tyr-Cys--.

Signed and Sealed this

Twenty-ninth Day of May, 2001

Attest:

NICHOLAS P. GODICI

*Attesting Officer*  *Acting Director of the United States Patent and Trademark Office*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 51 amino acids
( B ) TYPE: amino acid
( C ) STRANDEDNESS: single
( D ) TOPOLOGY: linear ( x i ) SEQUENCE DESCRIPTION: SEQ ID NO:1:

```
Ala  Thr  Tyr  Asn  Gly  Lys  Cys  Tyr  Lys  Lys  Asp  Asn  Ile  Cys  Lys  Tyr
 1              5                        10                       15
Lys  Ala  Gln  Ser  Gly  Lys  Thr  Ala  Ile  Cys  Lys  Cys  Tyr  Val  Lys  Lys
              20                        25                       30
Cys  Pro  Arg  Asp  Gly  Ala  Lys  Cys  Glu  Phe  Asp  Ser  Tyr  Lys  Gly  Lys
              35                        40                       45
Cys  Tyr  Cys
     50
```

( 2 ) INFORMATION FOR SEQ ID NO:2:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( x i ) SEQUENCE DESCRIPTION: SEQ ID NO:2:

```
Cys  Tyr  Lys
 1
```

( 2 ) INFORMATION FOR SEQ ID NO:3:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( x i ) SEQUENCE DESCRIPTION: SEQ ID NO:3:

```
Cys  Pro  Arg  Asp  Gly  Ala  Lys
 1                    5
```

( 2 ) INFORMATION FOR SEQ ID NO:4:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:4:

```
Thr  Ala  Ile  Cys  Lys
 1                 5
```

( 2 ) INFORMATION FOR SEQ ID NO:5:

( i ) SEQUENCE CHARACTERISTICS:
( A ) LENGTH: 4 amino acids
( B ) TYPE: amino acid
( C ) STRANDEDNESS: single
( D ) TOPOLOGY: linear (x i) SEQUENCE DESCRIPTION: SEQ ID NO:5:

Cys Tyr Val Lys
1

(2) INFORMATION FOR SEQ ID NO:6:

(i) SEQUENCE CHARACTERISTICS:
(A) LENGTH: 5 amino acids
(B) TYPE: amino acid
(C) STRANDEDNESS: single
(D) TOPOLOGY: linear (x i) SEQUENCE DESCRIPTION: SEQ ID NO:6:

Asp Asn Ile Cys Lys
1               5

(2) INFORMATION FOR SEQ ID NO:7:

(i) SEQUENCE CHARACTERISTICS:
(A) LENGTH: 7 amino acids
(B) TYPE: amino acid
(C) STRANDEDNESS: single
(D) TOPOLOGY: linear (x i) SEQUENCE DESCRIPTION: SEQ ID NO:7:

Cys Glu Phe Asp Ser Tyr Lys
1               5

(2) INFORMATION FOR SEQ ID NO:8:

(i) SEQUENCE CHARACTERISTICS:
(A) LENGTH: 3 amino acids
(B) TYPE: amino acid
(C) STRANDEDNESS: single
(D) TOPOLOGY: linear (x i) SEQUENCE DESCRIPTION: SEQ ID NO:8:

Cys Tyr Cys
1